United States Patent [19]
Johnston et al.

[11] Patent Number: 5,204,004
[45] Date of Patent: Apr. 20, 1993

[54] METHOD AND APPARATUS FOR PREVENTING BACTERIOLOGICAL CONTAMINATION BY A DENTAL TOOL WATER LINE

[76] Inventors: Simon E. Johnston; Anna M. Johnston, both of 9039 Juanita Dr. NE., Kirkland, Wash. 98033; Jeffrey F. Williams, 5690 W. Columbia Rd., Mason, Mich. 48854

[21] Appl. No.: 891,440

[22] Filed: May 29, 1992

[51] Int. Cl.⁵ .......................................... A61G 17/02
[52] U.S. Cl. ................................. 210/651; 210/652; 210/541; 433/80
[58] Field of Search ............... 433/80, 25, 89, 229; 210/321.6, 321.72, 321.75, 321.84, 541, 542, 634, 644, 649-652

[56] References Cited

PUBLICATIONS

Infection Control 91 Report, Infection-Control Products and News for the Dental Profession, "Infection Control Conference Highlights Practice, Research, & Industry Concerns," Dental Products Report, Sep. 1991, pp. 92 and 98.

*Primary Examiner*—Frank Sever
*Attorney, Agent, or Firm*—Christensen, O'Connor, Johnson & Kindness

[57] ABSTRACT

A method and apparatus are disclosed for preventing bacterial contamination from being introduced into a dental patient's mouth by water flowing through a dental tool water line. A flexible water line typically used for supplying water to a dental syringe, high-speed hand piece, or ultrasonic scaler has been found to support and encourage the growth of a significant biofilm that serves as a source of bacteria. To prevent the bacteria from being introduced into a patient's mouth by water flowing through the line, and thus into the patient's system, an in-line water filter is installed within the water line supplying water to the dental tool, at a point adjacent thereto. Conventional Luer fittings on the in-line water filter facilitate its quick installation and replacement. In addition, a cap protects the sterility of the outlet port of the in-line water filter during the installation process. The in-line water filter includes a microporous membrane that blocks bacteria and other particulate matter larger than approximately 0.2 microns, so that water flowing from the outlet port of the in-line water filter is substantially sterile.

20 Claims, 1 Drawing Sheet

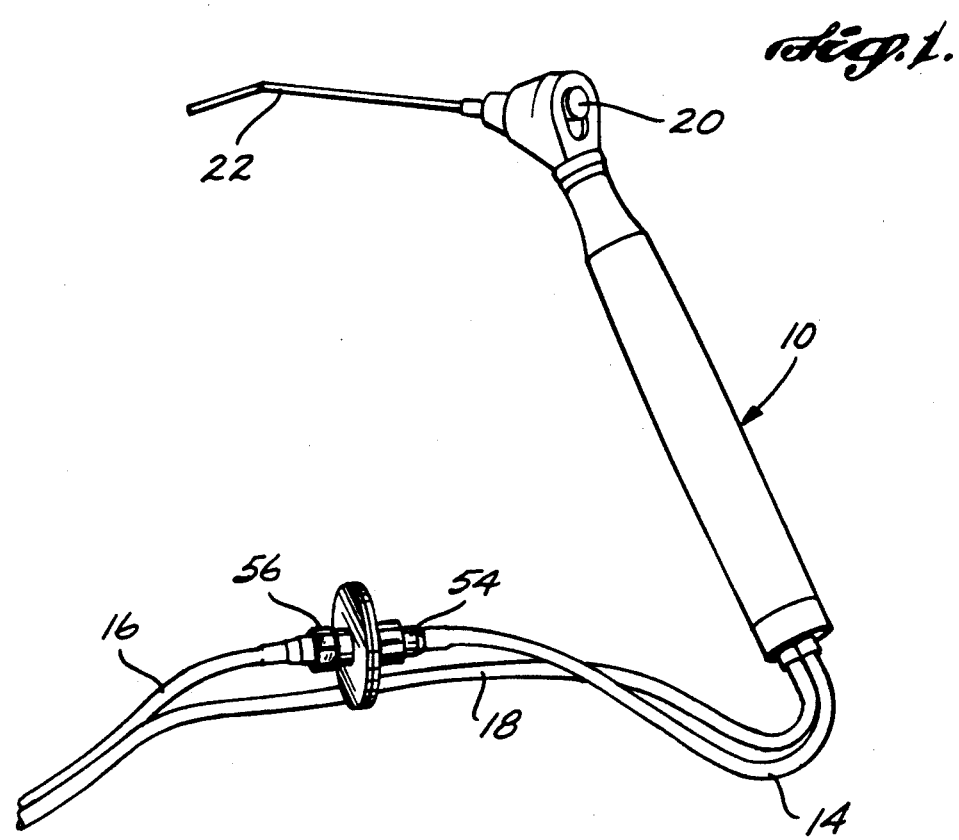
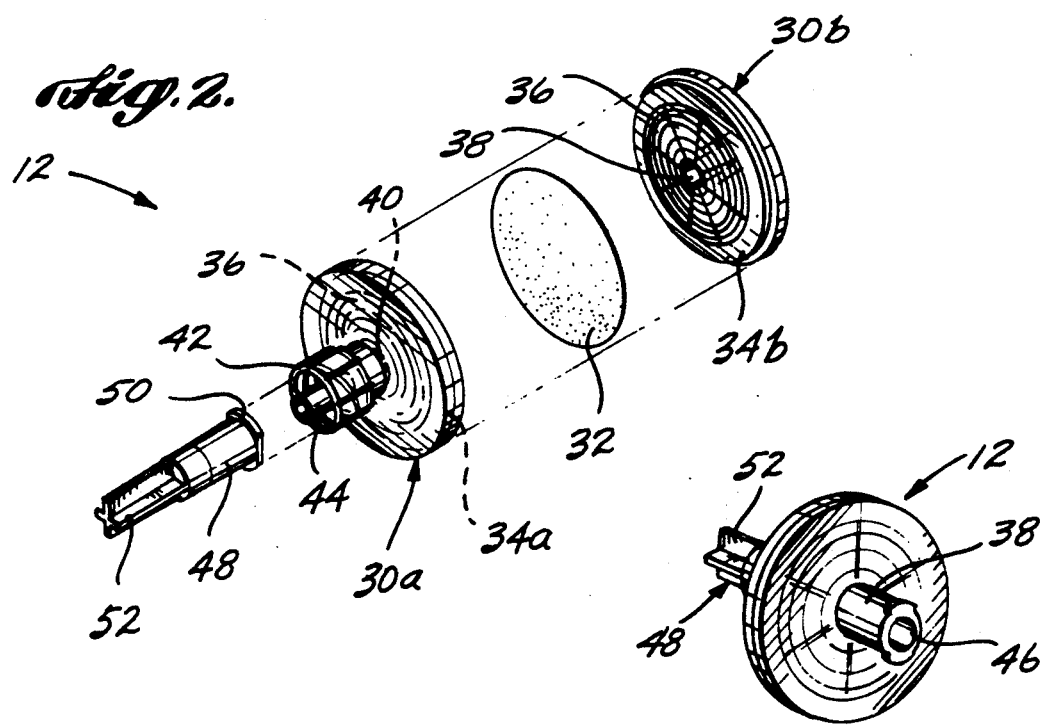

METHOD AND APPARATUS FOR PREVENTING BACTERIOLOGICAL CONTAMINATION BY A DENTAL TOOL WATER LINE

FIELD OF THE INVENTION

The present invention generally relates to a water filter, and more specifically, to an in-line filter for filtering bacteriological contaminants from a water stream.

BACKGROUND OF THE INVENTION

Many dental procedures are made less painless and more efficient by the use of dental tools that employ a small volume of water, which is injected into a patient's mouth. For example, high-speed handpieces used for intra-oral drilling and grinding are typically cooled by a small stream of water, thereby minimizing at least some of the discomfort produced by heat that is generated thereby. Even simple cleaning procedures that produce bits of scale and tartar require that the debris be flushed from the work site and expectorated from the mouth with water injected through an air/water syringe. Ultrasonic scaling equipment also employs water injected into a patient's mouth. The source of the water used in each of these devices is normally city tap water that is conveyed from a dental workstation to the dental tool through an elastomeric or flexible plastic line. Although a city tap water supply may be chlorinated to disinfect it when drawn from the city's reservoir or storage tank, the water is not sterile when it is delivered to the patient's mouth.

Investigation has revealed that a biofilm often is present along the inner surface of the elastomeric plastic water line used to convey water from the dental workstation to a dental tool. Water flowing through this line develops a relatively high bacterial count by picking up bacteria from the biofilm. Because it is not unusual for dental procedures to cause bleeding in a patient's mouth, there is thus a high probability that the bacteria from the biofilm in the water line will enter a patient's blood stream. In healthy individuals, a small infusion of bacteria may not be cause for concern, since their bodies' natural immune systems can deal with the infection. However, people who are weakened because of prior or current health problems are particularly susceptible to illness caused by such bacteria. In fact, even healthy people can be infected and become ill due to exposure to the very high bacterial counts often found in water delivered through dental tool water lines. As noted in a study done by Chris Miller, Ph.D., described in an article entitled *Infection Control 91 Report*, pp. 92–93, Dental Products Report, September 1991, the bacteria found in the water lines include a number of potentially harmful nosocomial disease agents, including *Legionella pneumophila*, *Pseudomonas aeruginosa*, *Pseudomonas cepacia*, Flavobacterium spp, *Mycobacterium chelonae*, Acinetobacter spp, *Klebsiella pneumoniae*, and Acanthamoeba.

While it is possible to sterilize a dental tool water line with a sterilizing fluid, the biofilm is extremely difficult to completely remove and tends to quickly reestablish itself. Furthermore, the biofilm tends to impede the disinfectant action. Accordingly, the bacterial count in water delivered to a patient's mouth rapidly increases to unacceptable levels. Unfortunately, this problem was previously unrecognized by dental professionals. It is not an obvious problem, since most people would not associate an illness that they subsequently experienced with an infection caused by microorganisms delivered in water previously injected into their mouths during a dental procedure a week or two before. Because the bacterial infection problem associated with dental tool water lines has not been earlier recognized, there is not an available solution to the problem that is sufficiently low in cost to encourage dentists to employ it.

SUMMARY OF THE INVENTION

In accordance with the present invention, apparatus is defined for use in connection with dental tools that employ a water line for conveying water to a patient's mouth, to protect the patient from bacteriological contamination due to bacteria that may be growing in the water line. The apparatus includes a housing in which are formed an inlet port and an outlet port. Prior to use and installation of the apparatus, the outlet port is in a sterile condition. A quick-connect inlet fitting is formed on the inlet port, and another on the outlet port. Disposed within the housing is a microporous membrane having a porosity selected to block a predefined size of particulate matter, including bacteria, without significantly restricting water flow through the membrane. This membrane sealingly extends between an internal periphery of the housing so that all water flowing in the inlet port must pass through the membrane before flowing out of the outlet port. A sterile cap that is sized to fit over the outlet port protects it from being contaminated by exposure to a non-sterile environment before use, for example, when it is handled during installation of the apparatus in the water line. The apparatus is intended for installation in a water line that has an internal surface capable of supporting a bacterial growth, i.e., a biofilm, so that bacteria in the water entering the inlet port are blocked and prevented from reaching a patient's mouth through a dental tool, such as a syringe, high-speed handpiece, or ultrasonic scalar that is connected to the outlet port. As a result, a patient is protected from exposure to potentially harmful bacteria that might cause illness.

Preferably, the quick-connect inlet and outlet fittings are Luer fittings of a conventional style used on medical apparatus. The sterile cap has opposed distal ends, one of which includes a flange sized to engage the Luer fitting at the outlet port. The other distal end of the cap includes means for enhancing a user's grip on the cap to facilitate decoupling and removal of the cap from the Luer fitting during installation of the apparatus into a water line. The means for enhancing a user's grip on the cap also enable the apparatus to be more readily rotated to connect a mating Luer fitting on the water line to the Luer fitting at the inlet port. The sterile cap is then removed to enable a user to connect a mating Luer fitting to the fitting at the outlet port, without contaminating the outlet port.

A retrofit kit is also included with the apparatus for modifying an existing water line coupled to a dental tool so that it includes quick-connect fittings. These fittings are installable on ends of the water line after it is cut adjacent to a dental tool. The retrofit kit thus adapts an existing water line to couple with the housing, by providing the quick-connect fittings on the ends of the water line for connection with the quick-connect fittings on the housing. Instructions are included that define how a user should install the retrofit kit to enable use of the apparatus to filter bacteria from a water line carrying water to a dental tool.

In the preferred form of the apparatus, the housing has an oblate round shape, and the inlet port and the outlet port are substantially centered within opposed surfaces of the housing. The membrane is substantially planar and round. First and second disk-like portions comprising the housing are sealed together around a periphery of the membrane so that it is sealingly disposed between the two portions. The quick-connect fittings extend outwardly in opposite directions from the first and second portions at the inlet and outlet ports.

A method for minimizing bacteriological contamination of a patient's mouth from bacteria that may be present in a water line coupled to a dental tool comprises another aspect of this invention. The steps of the method are generally consistent with the functions of the components comprising the apparatus discussed above.

The foregoing aspects and many of the attendant advantages of this invention will become more readily appreciated as the same becomes better understood by reference to the following detailed description, when taken in conjunction with the accompanying drawings.

BRIEF DESCRIPTION OF THE DRAWINGS

FIG. 1 is an isometric view of a dental tool and a portion of its water line in which apparatus in accordance with the present invention are installed;

FIG. 2 is an exploded view of an in-line water filter used to block bacteria in water flowing through a dental tool water line, and a cap that protects an outlet port of the water filter; and FIG. 3 is an isometric view of the inlet side of the in-line water filter.

DETAILED DESCRIPTION OF THE PREFERRED EMBODIMENT

In FIG. 1, a typical dental syringe 10 is shown retrofitted with an in-line water filter 12 in accordance with the present invention. In-line water filter 12 is coupled to dental syringe 10 by a relatively short section of pre-sterilized water line 14, which normally comprises a polyvinyl or other type of plastic. Virtually all such flexible water lines have a biofilm on their internal surfaces. As noted above, the presence of this biofilm in the water line serves as a source of potentially harmful bacteria. Accordingly, in-line water filter 12 is installed in the water line so that it is approximately 3 to 5 inches upstream of dental syringe 10. A substantially longer section of water line 16 extends from in-line water filter 12 to a source of city tap water provided from a dental workstation (not shown). Dental syringe 10 is also supplied with compressed air from the dental workstation through an air line 18. A slide selector valve 20 enables a user of dental syringe 10 to selectively control the flow of either a compressed air stream or water through a nozzle 22 into a patient's mouth (not shown).

Prior to installation of in-line water filter 12, the biofilm growing on the internal surfaces of the water line tends to infect water flowing through the line with bacteria, which are then injected into the patient's mouth during use of dental syringe 10. Introduction of such bacteria into the patient's mouth after a dental procedure is performed on the patient that causes intra-oral bleeding can enable the bacteria to enter the patient's blood stream, and may subsequently lead to illness caused by the bacteria. However, after installation of in-line water filter 12, bacteria carried by the water flowing through water line 16 are substantially blocked at the in-line water filter 12, so that the bacterial count in water flowing through the relatively short section of water line 14 into the patient's mouth is sufficiently low to justify labeling the water as "sterile," consistent with the accepted medical definition of that term. A patient receiving water intra-orally through nozzle 22 after installation of in-line water filter 12 is thus protected from any significant introduction of bacteria from a biofilm in the relatively longer section of water line 16. As a result, the risk of bacterial infection due to bacteria in the water stream introduced into the patient's mouth during dental procedures is virtually eliminated.

In FIGS. 2 and 3, details of in-line water filter 12 are shown, prior to its installation in the water line supplying dental syringe 10. The in-line water filter comprises two oblate or flattened disk-shaped sections 30a and 30b that are bonded together around their periphery. A microporous membrane having a porosity that blocks the passage therethrough of particulate matter having a diameter larger than approximately 0.2 microns is sealingly disposed between housing sections 30a and 30b. The porosity of microporous membrane 32 is thus sufficiently low to block substantially all harmful bacteria, yet does not significantly inhibit the flow of water through the membrane. The periphery of microporous membrane 32 is sealingly compressed between annular compression flanges 34a and 34b of housing sections 30a and 30b, respectively. The outer portions of annular compression flanges 34 are cemented or ultrasonically welded together, thereby fixing the microporous membrane between the two housing sections and sealing it in place around its perimeter.

Housing section 30b includes an inlet port 38 that is substantially centered within it. A plurality of radial ribs 36 extend from inlet port 38 to annual compression flange 34b. Similarly, housing section 30a includes an outlet port 40 centered within it and also includes ribs 36 that extend radially from outlet port to annular compression flange 34a. Water entering inlet port 38 spreads outwardly over the surface of microporous membrane 32 between ribs 36, passes through the filter, and then collects toward outlet port 40, flowing between ribs 36 that are disposed on the inner surface of housing section 30a. Since microporous membrane 32 is sealed around its perimeter by annular compression flanges 34a and 34b, all water passing through housing sections 30a/b from inlet port 38 to outlet port 40 must pass through the microporous membrane. However, bacteria and other particulate matter larger than approximately 0.2 microns are blocked by microporous membrane 32 and thus prevented from exiting through outlet port 40.

Extending outwardly from outlet port 40 is a female Luer fitting 42 of generally conventional design. Water passing through outlet port 40 flows through an internal tubular portion 44 of the female Luer fitting. As shown in FIG. 3, a male Luer fitting 46 extends outwardly from inlet port 38 and is also of generally conventional design.

Since microporous membrane 32 can eventually become clogged with particulate matter, it is recommended that it be replaced on a periodic basis before the flow of water through the membrane is significantly inhibited by collected debris on its inlet side. Since most dental tools that introduce water into a patient's mouth do so at a relatively low flow rate, the effect on water flow to the dental tool caused by an initial installation of in-line water filter 12 is generally not perceptible until the microporous membrane has become significantly covered with bacterial and particulate debris on the inlet side. Luer fittings 42 and 46 facilitate the convenient replacement of in-line water filter 12, encouraging its replacement and disposal on a relatively frequent periodic basis. In addition, since in-line water filter 12 is of relatively low cost, dentists are encouraged to make use of the device to protect their patient's health by preventing bacterial infection due to water-borne bacteria that might otherwise occur.

As packaged for installation, in-line water filter 12 includes a cap 48 that is fitted over tubular portion 44 of Luer fitting 42 to protect the sterility of outlet port 40. Bacterial contamination of inlet port 38 prior to and during installation of the in-line water filter is not considered a potential problem, since microporous membrane 32 should block any contamination introduced by the user during the installation process, as long as the contamination is limited to the inlet port and male Luer fitting 46. Thus, as packaged and supplied to a user, at least outlet port 40, tubular portion 44 of Luer fitting 42, and the interior of housing section 34a are in a sterile condition. Cap 48 protects the sterility of the outlet port during handling by a user while installing the in-line water filter. A flange 50 that mates with female Luer fitting 42 enables cap 48 to be rotatably threaded into Luer fitting 42 and secured in place over interior tubular portion 44. At the opposite end from flange 50, cap 48 includes a plurality of longitudinally extending ribs 52 that enhance a user's grip on the cap while handling and rotating it and in-line water filter 12 during the installation process. In addition, longitudinally extending ridges 52 can be more readily gripped to remove cap 48 by twisting it out of female Luer fitting 42 once male Luer fitting 46 has been engaged with water line 16. Outlet port 40, and internal tubular portion 44 of female Luer fitting 42 are therefore only briefly exposed to the environment prior to being coupled to relatively short water line 14 during the installation process.

As noted above, in-line water filter 12 is generally intended as a retrofit to an existing dental tool water line. Although dental syringe 10 is shown in FIG. 1 as an exemplary dental tool with which the present invention is used, it should be clear that it can be used with other dental tools such as high-speed hand pieces and ultrasonic scalers. These dental tools also use flexible water lines that are subject to the growth of a bacterial biofilm and thus represent a potential source of bacterial infection from water-borne bacteria carried into a patient's mouth. Accordingly, the present invention is intended for use in virtually any dental tool water line to protect against this potential hazard.

To retrofit the water line supplying a flow of water to such a dental tool, it is cut at a point from 3 to 5 inches upstream of the dental tool, and the relatively short section of water line corresponding to water line 14 in FIG. 1 is flushed with a sterilizing fluid of the type commonly used by dentists for sterilizing equipment. Alternatively, the relatively short section of water line can be replaced with a new sterile section. A male fitting 54, as shown in FIG. 1, is then installed on the cut end of the relatively short section of water line. Similarly, a female Luer fitting 56 is installed on the cut end of the relatively longer section of water line that supplies water from a source. Male Luer fitting 54 and female Luer fitting 56 thus readily mate with the respective corresponding female and male Luer fittings 42 and 46 on in-line water filter 12. Cap 48 protects the sterility of outlet port 40 and interior tubular portion 44 of female Luer fitting 42 during this installation.

To facilitate the retrofit process, instructions (not shown) are included with in-line water filter 12 that explain how the in-line water filter should be installed. In addition, a retrofit kit comprising male Luer fitting 54 and female Luer fitting 56 is provided with the instructions to facilitate the initial installation of the in-line water filter within an existing dental tool water line.

While the preferred embodiment of the invention has been illustrated and described, it will be appreciated that various changes can be made therein without departing from the spirit and scope of the invention. Accordingly, the scope of the invention should be determined entirely by reference to the claims that follow.

The embodiments of the invention in which an exclusive property or privilege is claimed are defined as follows:

1. Apparatus for use in connection with dental tools that employ a water line for conveying water to a patient's mouth, said apparatus protecting a patient from bacteriological contamination that may be present in the water line, comprising:
   (a) a housing in which are formed an inlet port and an outlet port, said outlet port being in a sterile condition prior to use and installation of the apparatus in a water line;
   (b) a quick-connect inlet fitting formed on the inlet port;
   (c) a quick-connect outlet fitting formed on the outlet port;
   (d) means for bacteriological sterilization of water flow through the housing, including a microporous membrane having a porosity selected to block a predefined size of particulate matter, including bacteria, without substantially restricting water flow through the membrane, said membrane being disposed within the housing between the inlet port and the outlet port and sealingly extending between an internal periphery of the housing so that all water flowing in the inlet port passes through the membrane before flowing out the outlet port; and
   (e) a sterile cap sized to fit over the outlet port to protect it from being contaminated by exposure to a non-sterile environment when the housing is handled during installation in a water line, said apparatus being thus installable in a water line that has an internal surface capable of supporting a bacterial growth, so that bacteria within the water entering the inlet port are substantially blocked and prevented from reaching a patient's mouth through a dental tool used therein, said apparatus thereby protecting a patient from exposure to potentially harmful bacteria that might cause illness.

2. The apparatus of claim 1, wherein said quick-connect inlet and outlet fittings are Luer fittings.

3. The apparatus of claim 2, wherein the sterile cap has opposed distal ends, one distal end including a flange sized to engage the Luer fitting at the outlet port and the other distal end including means for enhancing a user's grip on the cap to facilitate decoupling and removal of the cap from the Luer fitting during installation of the apparatus into a water line supplying water to a dental tool.

4. The apparatus of claim 3, wherein the means for enhancing a user's grip on the cap enable the apparatus to be more readily rotated to connect a mating Luer fitting on a water line to the Luer fitting at the inlet port, said sterile cap being then removed to enable a user to connect a mating Luer fitting on a water line coupled to a dental tool to the Luer fitting at the outlet port, without contaminating the output port.

5. The apparatus of claim 1, further comprising a retrofit kit for modifying a water line coupled to a dental tool to include quick-connect fittings that are installable on ends of a water line cut adjacent to a dental tool, the quick-connect fittings thereby installed on each end of a water line that is thus cut mating with the quick-connect fittings on the inlet and the outlet ports, to adapt a water line to couple with the housing of the apparatus.

6. The apparatus of claim 5, further including instructions that define how a user should install the retrofit kit to enable use of the apparatus to filter bacteria from a line carrying water to a dental tool.

7. The apparatus of claim 1, wherein the housing has a substantially oblate-round shape, the inlet port and the outlet port being substantially centered within opposed surfaces of the housing.

8. The apparatus of claim 7, wherein the membrane is substantially planar and round, said housing comprising a first disk-like portion and a second disk-like portion that are sealed together around a periphery of the membrane, said membrane being thus sealingly disposed between the first and second portions, said quick-connect fittings extending outwardly in opposite directions from the first and second portions at the inlet and the outlet ports.

9. A method for minimizing bacteriological contamination of a patient's mouth from bacteria that may be present in a water line supplying water to a dental tool used in the patient's mouth, comprising the steps of:
  (a) cutting the water line adjacent to the dental tool, leaving a relatively short section of the water line coupled to the dental tool;
  (b) installing a quick-connect fitting on each end of the water line where it was cut; and
  (c) installing means for bacteriologically sterilizing water flow to the dental tool, including an in-line water filter having quick-connect fittings that mate with those installed in the water line in step (b), said in-line water filter substantially blocking bacteria from a biofilm that may exist in the water line upstream of the in-line water filter from being carried by the water into a patient's mouth.

10. The method of claim 9, further comprising the step of sterilizing an interior of the relatively short section of water line adjacent to the dental tool prior to installing the mating quick-connect fitting so that any bacteriological contamination existing therein is substantially eliminated.

11. The method of claim 9, further comprising the steps of providing a sterile outlet port on the in-line water filter and protecting the sterility of the outlet port with a cap that is removed during the installation of the water filter in the water line.

12. The method of claim 11, wherein the step of installing the in-line water filter includes the step of grasping the in-line water filter by the cap and connecting the quick-connect fitting that is on an inlet port thereof with the mating quick-connect fitting on the end of the water line, removing the cap, and then connecting the quick-connect fitting that is on the outlet port to the mating quick-connect fitting on the end of the relatively short section of the water line coupled to the dental tool, the sterility of the outlet port and of water subsequently flowing therethrough being thereby maintained.

13. The method of claim 9, further comprising the step of periodically replacing the in-line water filter to insure substantially unrestricted flow of water therethrough.

14. A method of removing bacteriological contamination from water that flows through an elastomeric line to a dental tool to provide sterile water at a patient's mouth, said bacteriological contamination being substantially produced by a bacterial growth in a biofilm that may exist on an interior surface of the elastomeric line, comprising the steps of:
  (a) installing means for bacteriologically sterilizing water flow to the dental tool into the elastomeric line at a point adjacent to the dental tool, said means comprising a readily replaceable in-line filter, said in-line filter including a microporous membrane having a porosity selected to filter particles and harmful bacteria from water flowing therethrough without substantially restricting water flow therethrough;
  (b) sterilizing at least an outlet port of the in-line filter prior to its installation in the elastomeric line, said outlet port being coupled to the dental tool by a section of the elastomeric line that is in a sterile condition prior to installation of the in-line filter; and
  (c) maintaining the sterility of the outlet port during installation of the in-line filter by using a cap to enclose the outlet port until immediately prior to coupling the outlet port to the dental tool, said in-line filter substantially blocking bacteria introduced by any bacterial growth in the elastomeric line upstream of the in-line filter from being introduced into a patient's mouth by the water flowing through the elastomeric line to the dental tool.

15. The method of claim 14, further comprising the step of providing quick-connect fittings on the elastomeric line that are selected to mate with quick-connect fittings on the in-line filter, to facilitate installation and replacement of the in-line filter.

16. The method of claim 14, further comprising the step of replacing the in-line filter on a predefined schedule to prevent it from becoming clogged with particulate matter.

17. The method of claim 14, further comprising the step of circulating a sterilizing fluid through the elastomeric line prior to installation of the in-line filter, said sterilizing fluid substantially reducing a bacterial count in a biofilm on an internal surface of the elastomeric line.

18. The method of claim 14, further comprising the step of providing a plurality of ridges on an exterior portion of the cap to facilitate a user gripping it to rotate the in-line filter to couple it to the quick-connect fitting on the elastomeric line and to decouple the cap from the quick-connect fitting on the in-line filter.

19. The method of claim 14, further comprising the step of providing a fitting on the cap that mates with the quick-connect fitting on the outlet port of the in-line filter, so as to engage the cap on the outlet port.

20. The method of claim 14, wherein the dental tool is one of a group consisting of a syringe, a high-speed handpiece, and an ultrasonic scalar.

* * * * *